United States Patent [19]
Vangermain et al.

[11] 4,376,718
[45] Mar. 15, 1983

[54] PROCESS FOR ACTIVATING OR REACTIVATING ETHYLENE OXIDE SILVER SUBSTRATE CATALYSTS

[75] Inventors: Erwin Vangermain; Claus-Dieter Mengler, both of Marl, Fed. Rep. of Germany

[73] Assignee: Chemische Werke Hüls A.G., Marl, Fed. Rep. of Germany

[21] Appl. No.: 136,045

[22] Filed: Mar. 31, 1980

[30] Foreign Application Priority Data

Apr. 26, 1979 [DE] Fed. Rep. of Germany ....... 2916887

[51] Int. Cl.³ .................. B01J 23/96; B01J 23/66; B01J 23/02; C07D 301/10
[52] U.S. Cl. .................................... 252/416; 252/475; 252/476; 549/536
[58] Field of Search ................... 252/416, 411 R, 475, 252/476; 260/348.34, 348.35; 549/536

[56] References Cited

U.S. PATENT DOCUMENTS

| | | |
|---|---|---|
| 2,355,831 | 8/1944 | Voorhees ......................... 252/411 R |
| 2,799,687 | 7/1957 | Gould ................................ 252/476 |
| 3,793,231 | 2/1974 | Bergmann et al. ................. 252/476 |
| 3,962,136 | 6/1976 | Nielson ........................... 260/348.34 |
| 4,012,425 | 3/1977 | Nielson ........................... 260/348.34 |
| 4,039,561 | 8/1977 | Mitsvhata ....................... 260/348.34 |
| 4,066,575 | 1/1978 | Winnick ............................. 252/476 |
| 4,125,480 | 11/1978 | Maxwell ......................... 260/348.34 |
| 4,305,844 | 12/1981 | Vangermain et al. ............. 252/475 |
| 4,310,442 | 1/1982 | Vangermain et al. ............. 252/476 |

Primary Examiner—P. E. Konopka
Attorney, Agent, or Firm—Wells & Wells

[57] ABSTRACT

Process for activating or reactivating silver substrate catalysts having promoter metals used in the production of ethylene oxide by oxidizing ethylene with oxygen or with gases containing oxygen.

At least part of the mixture of reaction gases is made to pass at least in part through a bed arranged before the catalyst zone, this bed containing uniformly distributed compounds of the promoter metals.

8 Claims, 3 Drawing Figures

PROCESS FOR ACTIVATING OR REACTIVATING ETHYLENE OXIDE SILVER SUBSTRATE CATALYSTS

CROSS REFERENCES TO RELATED APPLICATIONS

Applicants claim priority under 35 USC 119 for application P 29 16 887.4, filed Apr. 26, 1979 in the Patent Office of the Federal Republic of Germany.

The application of Erwin Vangermain et al, entitled "Silver Catalysts for the Production of Ethylene Oxide", Ser. No. 135,927, filed Mar. 31, 1980 is incorporated herein to show the preparation of silver catalysts for use in the production of ethylene oxide.

BACKGROUND OF THE INVENTION

The field of the invention is the activation and reactivation of supported silver catalysts which are useful in the preparation of ethylene oxide by the catalytic vapor phase oxidation of ethylene.

The state of the art of processes for preparing ethylene oxide by the catalytic vapor phase oxidation of ethylene with molecular oxygen in the presence of supported silver catalysts may be ascertained by reference to U.S. Pat. Nos. 4,012,425 and 4,039,561, the disclosures of which are incorporated herein. U.S. Pat. Nos. 3,793,231; 3,962,136 and 4,066,575 disclose the state of the art of silver catalysts for the production of ethylene oxide, the disclosures of which are incorporated herein. The reactivation of silver catalysts is disclosed in U.S. Pat. Nos. 4,051,068 and 4,125,480, the disclosures of which are incorporated herein.

Silver catalysts are used in the preparation of ethylene oxide by oxidizing ethylene with oxygen or with gases containing oxygen. It is further known to react such catalysts with so-called promoters, especially the alkali earth metal compounds, preferably barium compounds and/or alkali metal compounds. In particular, the use of heavy alkali metals, rubidium and/or cesium are known from U.S. Pat. Nos. 3,962,136; 4,066,575; 4,039,561. The promoters ordinarily are deposited on the substrate simultaneously with the silver or subsequent to the silver deposition in the preparation of the catalyst.

It is furthermore known that the silver catalysts lose selectivity in the course of time and that after a few years, catalysts must be replaced. The exchange of a catalyst which has lost some of its performance by a new one is time-consuming and is labor intensive in large-scale industrial plants. Furthermore, the exchange causes a production stoppage and high costs.

It is furthermore known to improve the performance of a silver catalyst or to reactivate a used one as disclosed in U.S. Pat. Nos. 4,125,480 and 4,051,068. This is done for instance in large-scale plants by flooding the catalyst-filled reactor with the solution of the promoter metal solution. Following separation of the excess solvent, the residual solvent is removed by heating the catalyst bed and blowing an inert gas through it. This procedure requires using solvents and again a stoppage in production.

SUMMARY OF THE INVENTION

Having in mind the limitations of the prior art it is an object of the present invention to improve catalyst output by a simpler treatment, to maintain catalyst output as long as possible, and to avoid exchanging catalysts for new ones or at least to delay such a step as long as possible.

The objects of the present invention are achieved by locating a bed containing promoter metal compounds in uniformly distributed form in front of the catalyst zone and then passing at least part of the mixture of reaction gases first through the bed and then second through the catalyst zone.

Advantageously, compounds of the promoter metals are used which are volatile under the conditions of reaction in the catalyst zone.

BRIEF DESCRIPTION OF THE DRAWINGS

The drawings appended hereto show two embodiments of the present invention, wherein.

DESCRIPTION OF THE PREFERRED EMBODIMENTS

The procedure of the present invention is applicable to both silver catalysts already containing promoters to keep up the output and to those catalysts which lack such promoters, in order to improve the performance.

The promoter metal compounds are used in coarse-grain form, in particular a substrate layer is used, which corresponds to the catalyst substrate that was impregnated with solutions of the promoter metal compounds.

Figure 1:
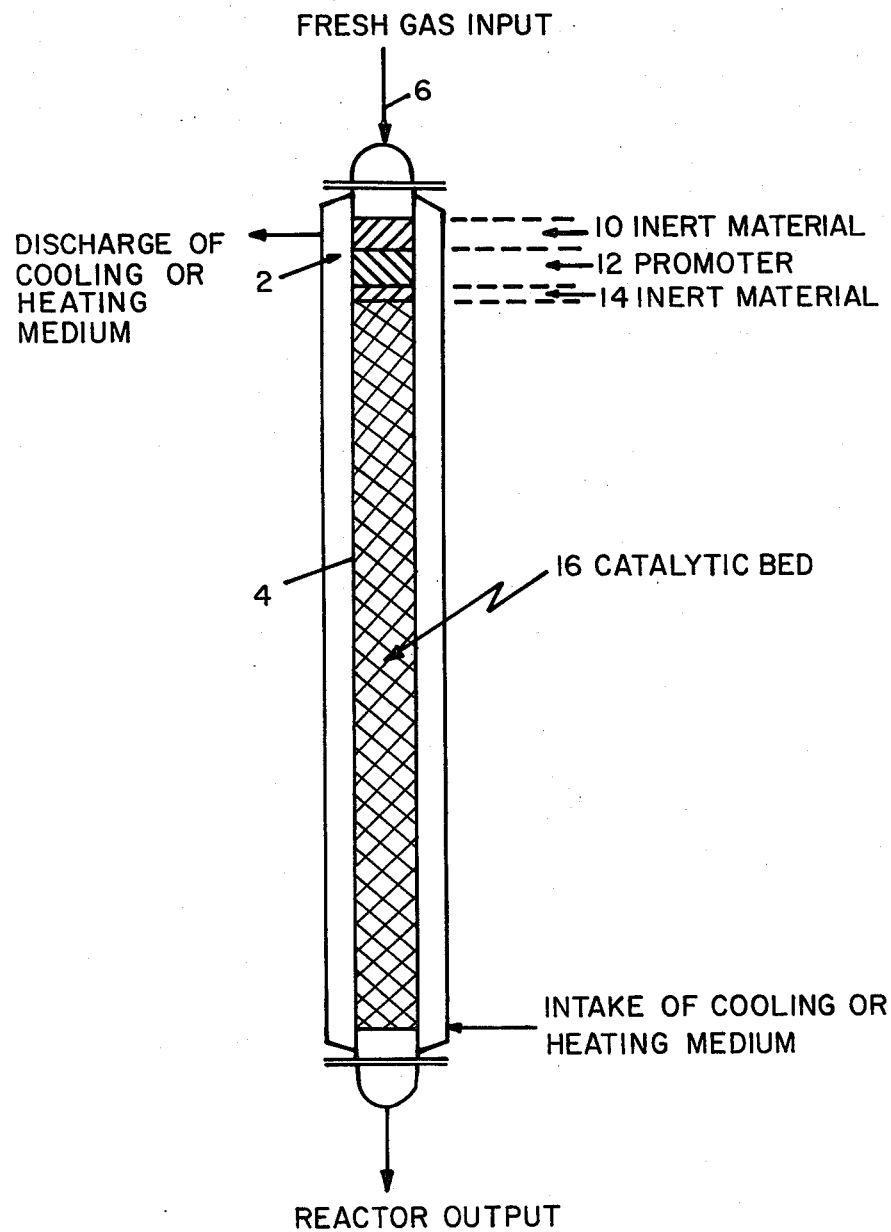
FIG. 1 is a flow sheet showing the promoter containing bed mounted directly into the reactor tubes at the beginning of the catalytic zone.
Figure 2:
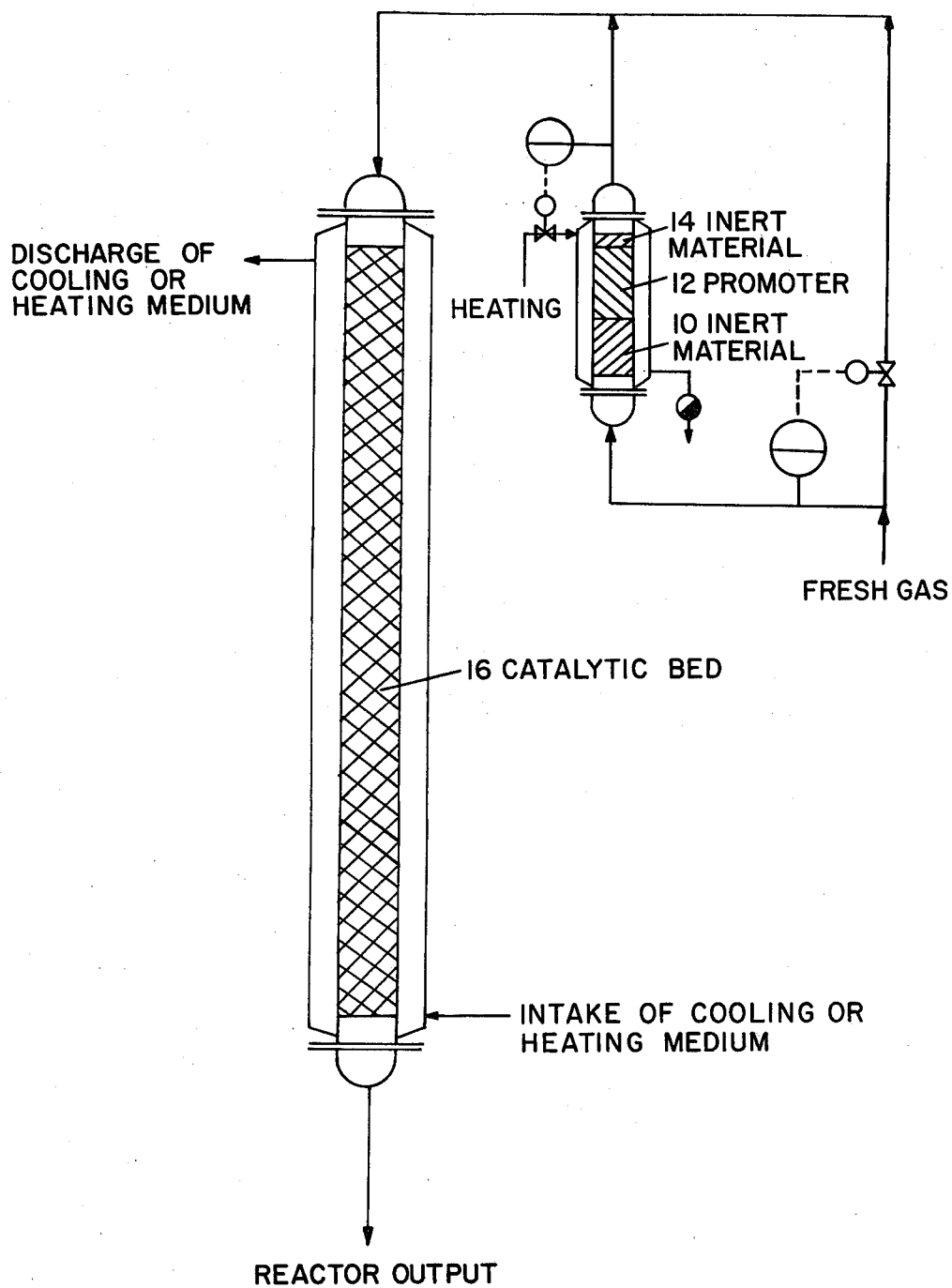
FIG. 2 is a flow sheet showing the promoter containing bed located in a separate container and in a partial flow of the reaction mixture of gases.
Figure 3:
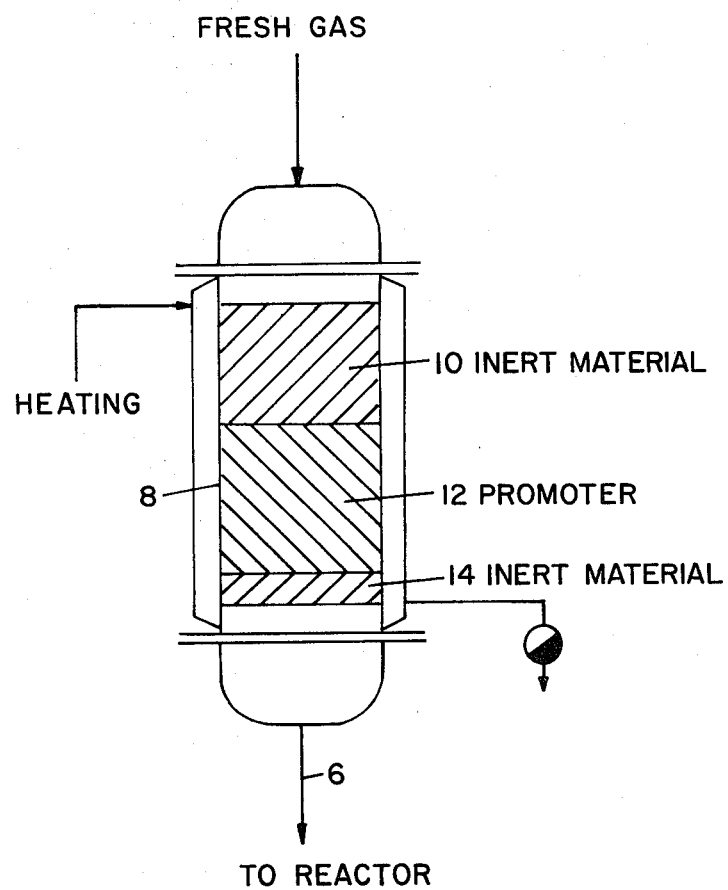
FIG. 3 is a detailed showing in cross section of the separate container of FIG. 2 showing the layers of pure substrate material, promoter metal compounds and further substrate layer.

As shown in FIG. 1 promoter containing bed 2 can be mounted directly into the individual reaction tubes 4 at the beginning of the catalytic zone, that is, at the intake end 6 of the reaction gas. It is also possible to so construct the bed that it can be easily exchanged. In a particular embodiment as shown in FIG. 3, the bed is located in a separate container 8 mounted in the embodiment as shown in FIG. 2, the container is located in a partial flow of the reaction gas, thereby offering the advantage that the partial flow need be operative only part of the time. Advantageously, the bed in the reaction tubes or in the separate containers are such that as particularly shown in FIG. 3 first there is a layer of pure substrate material 10, then a layer of the promoter metal compounds 12 or a substrate layer soaked with promoter metal compounds, and lastly, a further substrate layer 14.

Such an application offers the advantage that the reaction gas can be varied in its temperature during its transit. The container and the reaction tube are or can be adapted to corresponding heating and control means.

The proportion of the individual promoter metals are set to the desired ratios. The layer thickness of the substrate impregnated with promoter metal compounds in the reaction tubes as a rule is between 1 and 20, especially between 5 and 10% of the tube length.

Suitable promoter metal compounds are especially barium compounds such as barium oxide, barium peroxide, barium hydroxide, barium nitrite, barium nitrate, barium carbonate, barium acetate, barium oxalate, barium tartrate, barium naphthenate, barium stearate, barium dodecanate, barium chloride and/or alkali metal compounds such as those of rubidium and/or cesium, for instance oxides, peroxides, hydroxides, nitrites, nitrates, carbonates, acetates, oxalates, tartrates, stearates, dodecanates and chlorides.

The following specific examples further help to explain the present invention.

The reactor is a 6,000 mm long reaction tube which is 26 mm in diameter and is made of stainless steel. In each case, one tube was filled with a catalyst described in further detail in the examples below. A second tube 4, as shown in FIG. 1 always was filled with the same catalyst 16, and additionally a bed was mounted at the gas intake location consisting, as seen in the direction of the gas flow, of 400 mm of the untreated substrate material 10, 450 mm of a substrate coated with promoter metals 12 and 30 mm of untreated substrate 14. The tubes were encased by a jacket containing water or steam for removing the heat of reaction. The catalysts each contained 19.5% by weight of silver. The substrate material used was an aluminum oxide substrate containing about 12% by weight of silicon dioxide. The reaction tubes were operated simultaneously with the same gas mixture. This gas mixture was as follows:

| 25% | by volume of | $C_2H_4$ |
| 49% | by volume of | $CH_4$ |
| 6.8% | by volume of | $O_2$ |
| 4.5% | by volume of | $CO_2$ |
| 0.2% | by volume of | $C_2H_6$ |
| remainder | | $Ar + N_2$ |

EXAMPLE 1

2.4 kg of the silver catalyst as described above were used, without any additional promoters. The impregnated substrate layer in the second reaction tube contained 200 g of substrate material and 1.1 g of potassium, 1.6 g of barium and 0.34 g of cesium which had been deposited in the form of an aqueous solution of barium peroxide and cesium nitrate that had been made alkaline by means of potassium carbonate.

In both cases the gas applied at the end of the start-up phase was 9.26 m$^3$/l of catalysts (stp) at 19.8 bar gauge, corresponding to a total application of 25 m$^3$/h (stp). The chlorine content in the circulating gas was kept at 7–8 mg of Cl/m$^3$ (stp) using 1,2-dichloroethane. The steam chamber temperature was controlled in such a manner that an ethylene oxide concentration of 1.6% by volume on the average prevailed at the reactor discharge.

| | beginning | | after 6 weeks' operation | |
| --- | --- | --- | --- | --- |
| | selectivity mole % | temp. °C. | selectivity mole % | temp. °C. |
| Comparison | 74.0 | 254 | 71.6 | 271 |
| Invention | 74.3 | 252 | 74.8 | 251 |

EXAMPLE 2

The comparison catalyst used already contained 472 ppm of barium. Other conditions being equal, the following results were obtained:

| | beginning | | after 6 weeks' operation | |
| --- | --- | --- | --- | --- |
| | selectivity mole % | temp. °C. | selectivity mole % | temp. °C. |
| Comparison | 75.7 | 249 | 73.5 | 267 |
| Invention | 75.8 | 249 | 76.7 | 247 |

EXAMPLE 3

The comparison catalyst used already contained 481 ppm of barium and 91 ppm of cesium. Other conditions being equal, the following results were obtained;

| | beginning | | after 6 weeks' operation | |
| --- | --- | --- | --- | --- |
| | selectivity, mole % | temp. °C. | selectivity, mole % | temp. °C. |
| Comparison | 80.4 | 245 | 77.5 | 265 |
| Invention | 80.3 | 245 | 80.3 | 245 |

EXAMPLE 4

The comparison catalyst was a pure silver catalyst as in example 1. The substrate layer of the invention contained 0.29 g of rubidium in lieu of cesium. The following results were obtained:

| | beginning | | after 6 weeks' operation | |
| --- | --- | --- | --- | --- |
| | selectivity, mole % | temp. °C. | selectivity, mole % | temp. °C. |
| Comparison | 74.0 | 254 | 71.6 | 271 |
| Invention | 74.2 | 252 | 73.7 | 255 |

We claim:

1. In a process for activating or reactivating silver substrate catalysts having promoter metals therein used in the production of ethylene oxide by oxidizing a mixture of gases containing ethylene and an oxygen containing gas where the mixture of gases is passed over said silver substrate catalysts in a catalyst zone and defines a flow path, the improvement comprising:
locating a promoter bed containing uniformly distributed compounds of the promoter metals in at least a portion of said flow path of said mixture of gases and in front of said catalyst zone.

2. The process of claim 1, wherein said promoter metal compounds are deposited on a substrate material.

3. The process of claim 1, wherein said promoter metal compounds are deposited on a substrate material which is the same as that of the silver substrate catalyst.

4. The process of claim 1, wherein the compounds of the promoter metals are selected from compounds of potassium, rubidium, cesium, barium, or a mixture thereof.

5. The process of claim 1, wherein the bed containing the promoter metal compounds is located at the intake of the gases of reaction in a reaction tube along said flow path, said reaction tube containing said silver substrate catalysts.

6. The process of claim 5, wherein the bed containing the promoter metal compounds has a thickness which amounts to about 1 to 20% of the length of the reaction tube.

7. The process of claim 1, wherein said promoter bed has a first inert layer of inert material above and a second layer of inert material below said promoter bed.

8. The process of claim 5, wherein said promoter bed has a first layer of inert material above and a second layer of inert material below said promoter bed.

* * * * *